United States Patent
Ishibashi et al.

(10) Patent No.: US 7,192,137 B2
(45) Date of Patent: Mar. 20, 2007

(54) SPORTS GOGGLE

(75) Inventors: Fumio Ishibashi, Higashiosaka (JP);
Yoshihisa Ishiba, Higashiosaka (JP);
Eiji Shimizu, Takatsuki (JP); Hideya Takahashi, Kashiwara (JP)

(73) Assignee: Yamamoto Kogaku Co., Ltd., Osaka (JP)

( * ) Notice: Subject to any disclaimer, the term of this patent is extended or adjusted under 35 U.S.C. 154(b) by 0 days.

(21) Appl. No.: 10/497,648

(22) PCT Filed: Dec. 5, 2002

(86) PCT No.: PCT/JP02/12756

§ 371 (c)(1),
(2), (4) Date: Jun. 4, 2004

(87) PCT Pub. No.: WO03/047481

PCT Pub. Date: Jun. 12, 2003

(65) Prior Publication Data

US 2005/0225867 A1    Oct. 13, 2005

(30) Foreign Application Priority Data

Dec. 5, 2001   (JP) .............................. 2001-371721

(51) Int. Cl.
*G02C 7/02* (2006.01)
*G02B 27/14* (2006.01)

(52) U.S. Cl. .................. 351/159; 351/41; 351/158; 359/630

(58) Field of Classification Search ................ 359/630, 359/631; 351/41, 158, 159
See application file for complete search history.

(56) References Cited

U.S. PATENT DOCUMENTS

| | | | | |
|---|---|---|---|---|
| 4,869,575 A * | 9/1989 | Kubik | ............................ | 345/8 |
| 5,585,871 A * | 12/1996 | Linden | ........................ | 351/158 |
| 6,091,546 A * | 7/2000 | Spitzer | ........................ | 359/618 |
| 6,771,423 B2 * | 8/2004 | Geist | ........................... | 359/630 |
| 6,870,466 B2 * | 3/2005 | Rust et al. | .............. | 340/323 R |

FOREIGN PATENT DOCUMENTS

| | | |
|---|---|---|
| JP | 23020/1990 | 11/1991 |
| JP | 4-9166 | 1/1992 |
| JP | 5-146464 | 6/1993 |
| JP | 306956 | 11/1995 |
| JP | 8-285967 | 11/1996 |
| JP | 9-99125 | 4/1997 |
| JP | 2001/166148 | 6/2001 |
| WO | WO 92/08157 | 5/1992 |
| WO | WO 96/36404 | 11/1996 |

* cited by examiner

*Primary Examiner*—Scott J. Sugarman
(74) *Attorney, Agent, or Firm*—Koda & Androlia

(57) ABSTRACT

A sports goggle includes a goggle main body (1) on which information processing means (2) is mounted. The goggle main body (1) has an eye piece portion (3) on which information display means (4) is mounted. Information transmission means of transmission/reception of information on sports to/from outside can be mounted on the goggle main body (1). Furthermore, the information processing means (2) and the information display means (4) may be made as a unitary block. There is provided a sports goggle through which a user can check the displayed information even while performing a sport, can get information judged to be appropriate at appropriate moment in a comparatively short time, can pay attention to the display unit without lowering the sport ability, and can get sophisticated instructions from an instructor or a coach.

11 Claims, 7 Drawing Sheets

SPORTS GOGGLE

TECHNICAL FIELD

This invention relates to a pair of sports goggles with which during an exercise at a game an athlete can receive various sorts of information relating to the exercise or the game and instructions from instructors and/or coaches.

BACKGROUND ART

Athletes have conventionally been playing sports with sports goggles on. For example, it is scarcely surprising that swimmers are wearing swimming goggles to protect their eyes during practice or competitions. Marathon runners are also unsurprisingly wearing sunglasses to protect their eyes from the sun while running. Additionally, motorcycle racers are wearing motorcycle goggles to protect their eyes from wind pressure, dust and so on during practice runs or races.

These athletes sometimes receive instructions from instructors or coaches and/or receive information on the sports while playing the sports; however, in order to receive detailed instructions or information, they have to stop playing the sports, or the instructors or the coaches have to play along with them.

Therefore, to solve the above problem, radio transmission such as a FM transmitter and a CB (Citizens' Band) radio is used, so that it becomes possible for marathon runners and motorcycle racers to receive timely instructions or information aurally.

For swimmers, a simplified timekeeper which is designed to be mounted on the front face of swimming goggles is used to monitor the swimming time during a race so that they can learn their swimming time right after the race.

For divers, there is no other ways to get information during their diving but to look into an indicator which is provided separately from their diving masks, and this is the only means of receiving information for them.

However, the above conventional means of receiving information are hardly functional because the indicators are rather imprecise and in danger of coming off depending on the condition how the indicators are mounted on the body of athletes or goggles.

Additionally, there have been no indicators for diving which is capable of a display within a diving mask.

A spectacle-type display device, called a head-mounted display, which has already appeared on the market, has a displaying function. However, the device has the practical problems that it is uncomfortable to wear and difficult to play sports hard for a user because of the existence of wiring or the like for receiving information from the outside even though the user can check the display of the device.

Therefore, an object of the present invention is to solve the problems that the above conventional means of receiving information have and to provide sports goggles with which a user can check the displayed information as needed in order to get timely appropriate information in a relatively short time, can focus on the display without affecting the play of the sports and can receive detailed instructions from instructors and/or coaches while playing the sports.

DISCLOSURE OF INVENTION

In a pair of sports goggles of the present invention having a goggle main body, an information processing means and an information display means, the information processing means is mounted on the goggle main body and the information display means is mounted on an eyepiece portion of the goggle main body.

The pair of sports goggles of the present invention may further have an information communicating means of transmitting/receiving information on sports to/from the outside, and the information communicating means is mounted on the goggle main body.

In the pair of sports goggles of the present invention, the information processing means and the information display means may be integrally formed.

BEST MODE FOR CARRYING OUT THE INVENTION

As shown in FIGS. 1–5, a pair of sports goggles of the present invention has a goggle main body 1, an information processing means 2 and an information display means 4. The information processing means 2 is mounted on the goggle main body 1 and the information display means 4 is mounted on an eyepiece portion 3 of the goggle main body 1 so that a user can check the displayed information when necessary. The pair of sports goggles of the present invention further has an information communicating means (not shown in Figs.) of transmitting/receiving information on sports to/from the outside by digital or analog radio when necessary. The information communicating means is mounted on the goggle main body 1 so that a user can get timely appropriate information in a relatively short time. Accordingly, a user such as an athlete can check the information by focusing on the information display means 4 without stopping playing sports.

A microcomputer designed to be either fixed or removably mounted on the goggle main body 1 is adopted as the information processing means 2, and it houses a central processing unit (CPU), a random access memory (RAM), a read-only memory (ROM), a power source and so on therein, and is treated to be waterproofed, vibration-proofed and so on according to need. As the power source, a primary cell typified by a dry cell, a secondary cell typified by a nickel-cadmium cell, or the like may be used, but considering portability and economical efficiency, a secondary cell is preferable.

The information display means 4 includes a display device and an optical device. As the display device, a device which is small and can display high-density information, such as a liquid crystal, a cathode ray tube (CRT), a semiconductor device (LD), a light-emitting diode (LED), an electroluminescence (EL), a digital micromirror device (DMD) or the like, is generally used. As the optical device, imaging optics which is pre-designed to produce a virtual image before the user's eyes, such as a mirror, a prism, a lens, a holographic optical element (HOE) or the like is preferably used, but a retinal projection display which shows Maxwell View to the user and can be used without considering to distance perspective is more preferable.

The information processing means 2 and the information display means 4 may be two separate means, but it is more preferable to form them integrally in order to mount them neatly on the goggle main body 1 so that the pair of sports goggles can be worn with the good appearance.

The sports goggles of the present invention include the following diving mask, swimming goggles, sunglasses, motorcycle goggles or any other sports goggles.

Figure 1:
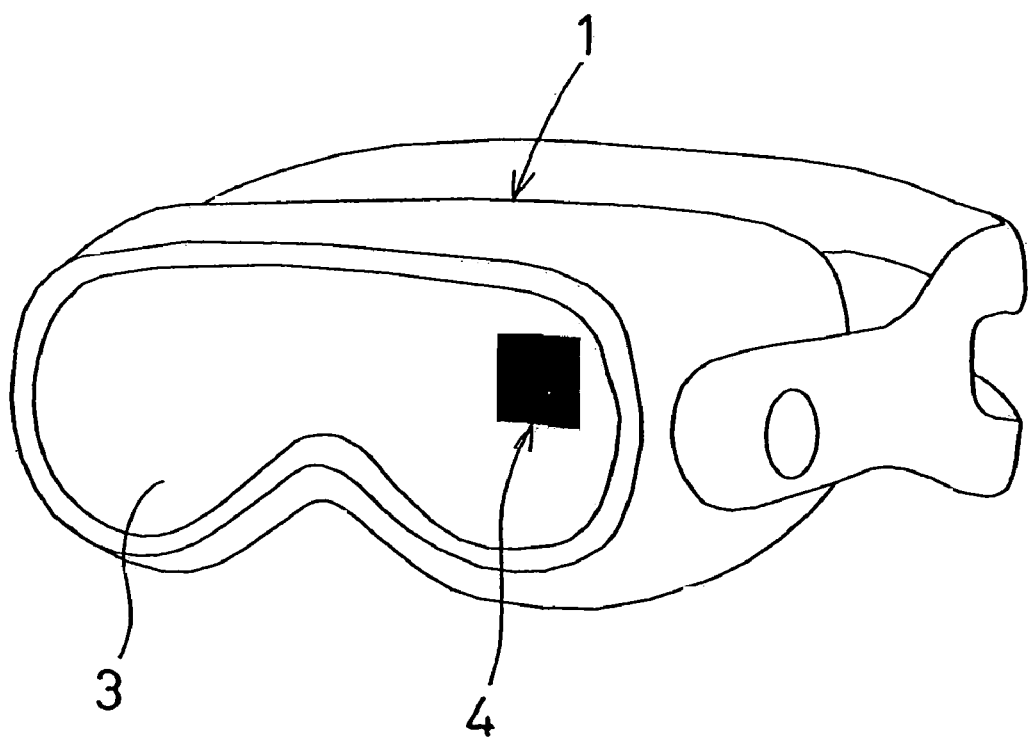
FIG. 1 is a perspective view showing an embodiment where a pair of sports goggles of the present invention is applied to a diving mask.
Figure 2:
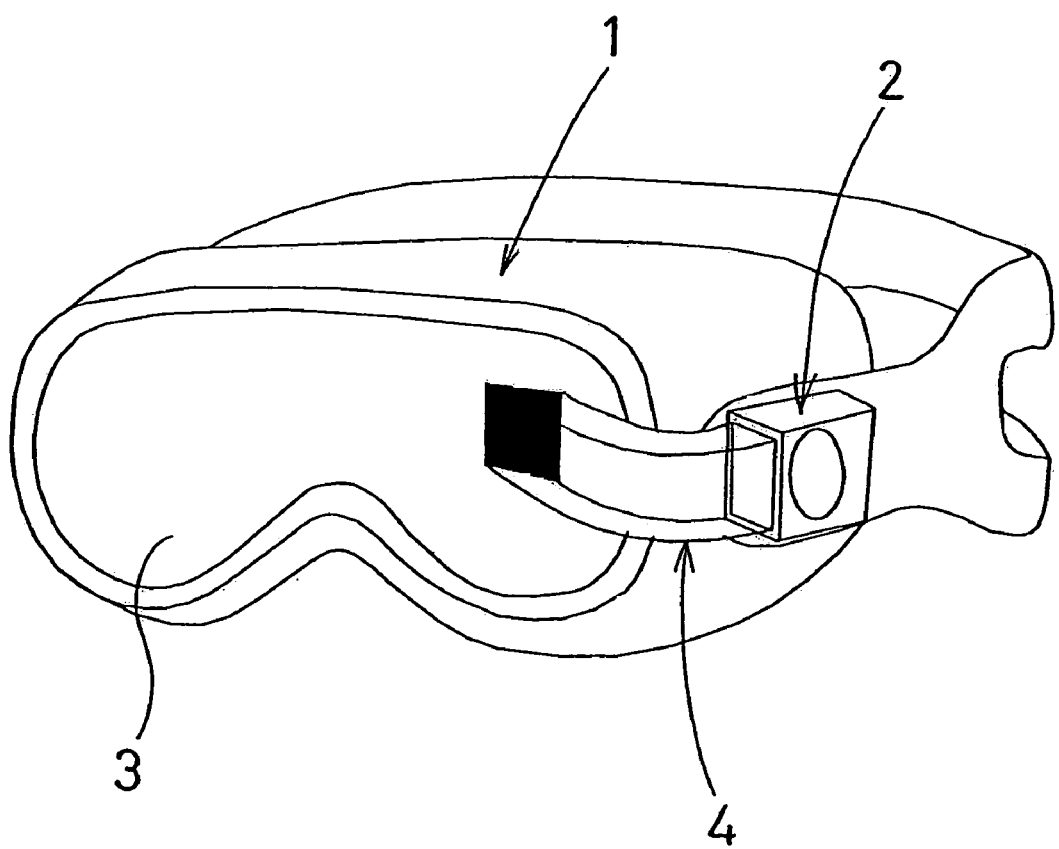
FIG. 2 is a perspective view showing another embodiment where a pair of sports goggles of the present invention is applied to a diving mask.

A pair of sports goggles of the present invention shown in FIG. 1 is used as a diving mask. The diving mask has a goggle main body 1, an information processing means 2 and an information display means 4. The information processing means 2 is mounted on the inner portion of the goggle main body 1 and the information display means 4 is mounted on the inner surface of a lens which is an eyepiece portion 3 of the goggle main body 1. The information processing means 2 and the information display means 4 of this diving mask are treated to be waterproofed, pressure-proofed and so on in order to make the diving mask operational underwater. In this pair of sports goggles as the diving mask, the information processing means 2 may be alternatively mounted on the outer portion of the goggle main body 1 and the information display means 4 is mounted on the outer surface of the lens, as shown in FIG. 2.

The information processing means 2 has a sensing function to check physiological information, temporal change in the depth of water, position and so on. It also has a navigation system using the undersea topographic information which is stored in the memory. Moreover, it may separately have a processing function to process a diving time, the residual pressure in a tank, a program for individual depressurization or the like.

The information display means 4 has a HOE which is laminated on a surface of the lens and a liquid crystal panel placed inside of the goggle so that a diver can see the information displayed on this liquid crystal panel.

These features enable a diver to work safely underwater.

Figure 3:
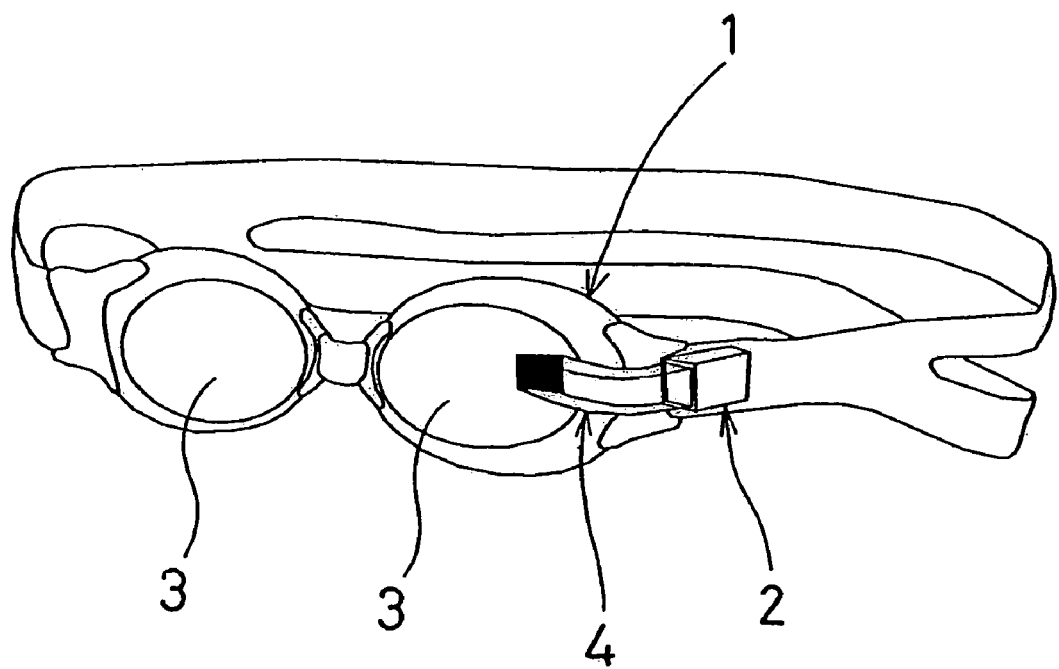
FIG. 3 is a perspective view showing another embodiment where a pair of sports goggles of the present invention is applied to a pair of swimming goggles.

A pair of sports goggles of the present invention shown in FIG. 3 is used as a pair of swimming goggles. The swimming goggles have a goggle main body 1, an information processing means 2 and an information display means 4. The information processing means 2 is mounted on the outer portion of the goggle main body 1 and the information display means 4 is mounted on a lens which is an eyepiece portion 3 of the goggle main body 1. The information processing means 2 and the information display means 4 of this pair of swimming goggles are treated to be waterproofed and so on in order to make the swimming goggles operational underwater.

The information processing means 2 has a sensing function to check physiological information, the velocity of water and so on. It also has an information communicating means for transmitting and receiving data instantly, and the information communicating means has a system for communicating with other outside transmitting and receiving devices. Moreover, it may separately have a processing function to process an elapsed time, a pace of swimming and so on.

The information display 4 has a HOE which is insert-molded on a surface of the lens and a liquid crystal panel placed inside of the goggle so that a swimmer can see the information displayed on this liquid crystal panel.

These features enable a swimmer to receive instructions from instructors and/or coaches and communicate with them while swimming.

Figure 4:
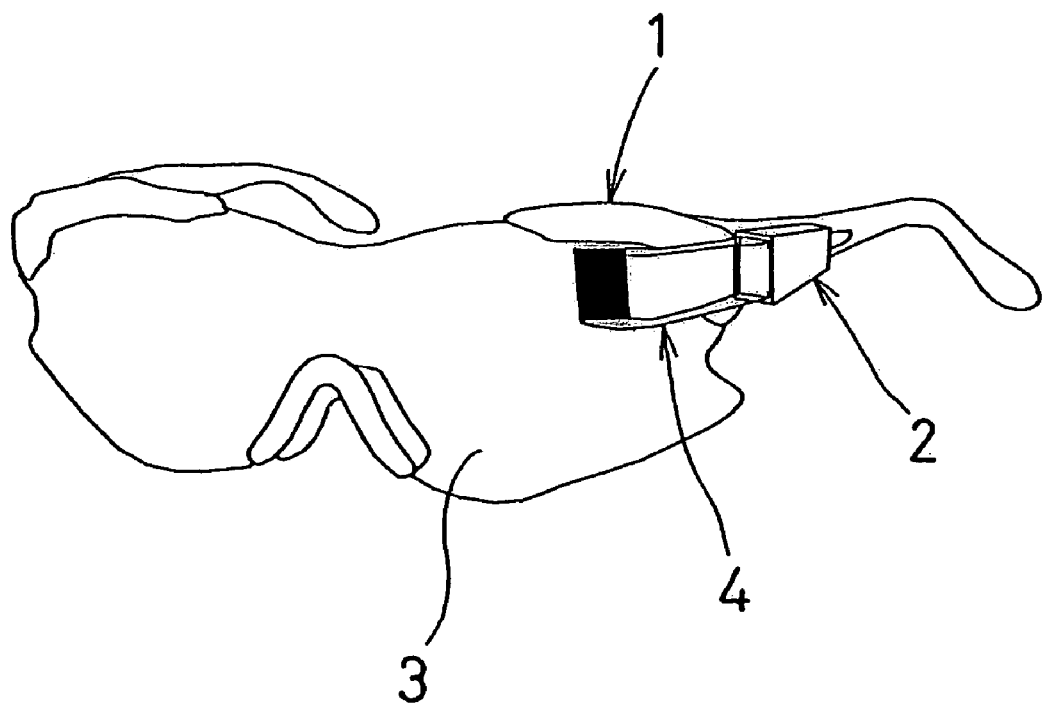
FIG. 4 is a perspective view showing another embodiment where a pair of sports goggles of the present invention is applied to a pair of sunglasses.

A pair of sports goggles of the present invention shown in FIG. 4 is used as a pair of sunglasses for marathon. The pair of sunglasses has a goggle main body 1, an information processing means 2 and an information display means 4. The information processing means 2 is mounted on the outer portion of the goggle main body 1 and the information display means 4 is mounted on a lens which is an eyepiece portion 3 of the goggle main body 1. The information processing means 2 and the information display means 4 of this pair of sunglasses are treated to be vibration-proofed, drip-proofed and so on in order to make the sunglasses operational while a user is running.

The information processing means 2 has a sensing function to check physiological information and the velocity of wind or the like. It also has an information communicating means for transmitting and receiving data instantly, and the information communicating means has a system for communicating with other outside transmitting and receiving devices. Moreover, it may separately have a processing function to process an elapsed time, a pace of running and so on.

The information display 4 has a lens which is integrally molded on a surface of the eyepiece portion 3 and a compact-sized cathode ray tube placed outside of the goggle main body 1 so that a marathon runner can see the information displayed by the compact-sized CRT.

These features enable a marathon runner to receive instructions from instructors and/or coaches and communicate with them while running. Moreover, if more than one runner is wearing this pair of sunglasses at the same time, it can be used for cooperation among the runners.

Meanwhile, in the case of the sunglasses for marathon, image data for reproducing virtual space may be set in the information processing means 2 and then displayed by the information display means 4 while running, for example, a marathon, so that a user runner can train in the virtual space where it seems as if the user is running with another runner as a pace maker or another runner to use tactics although the user is running alone.

Figure 5:
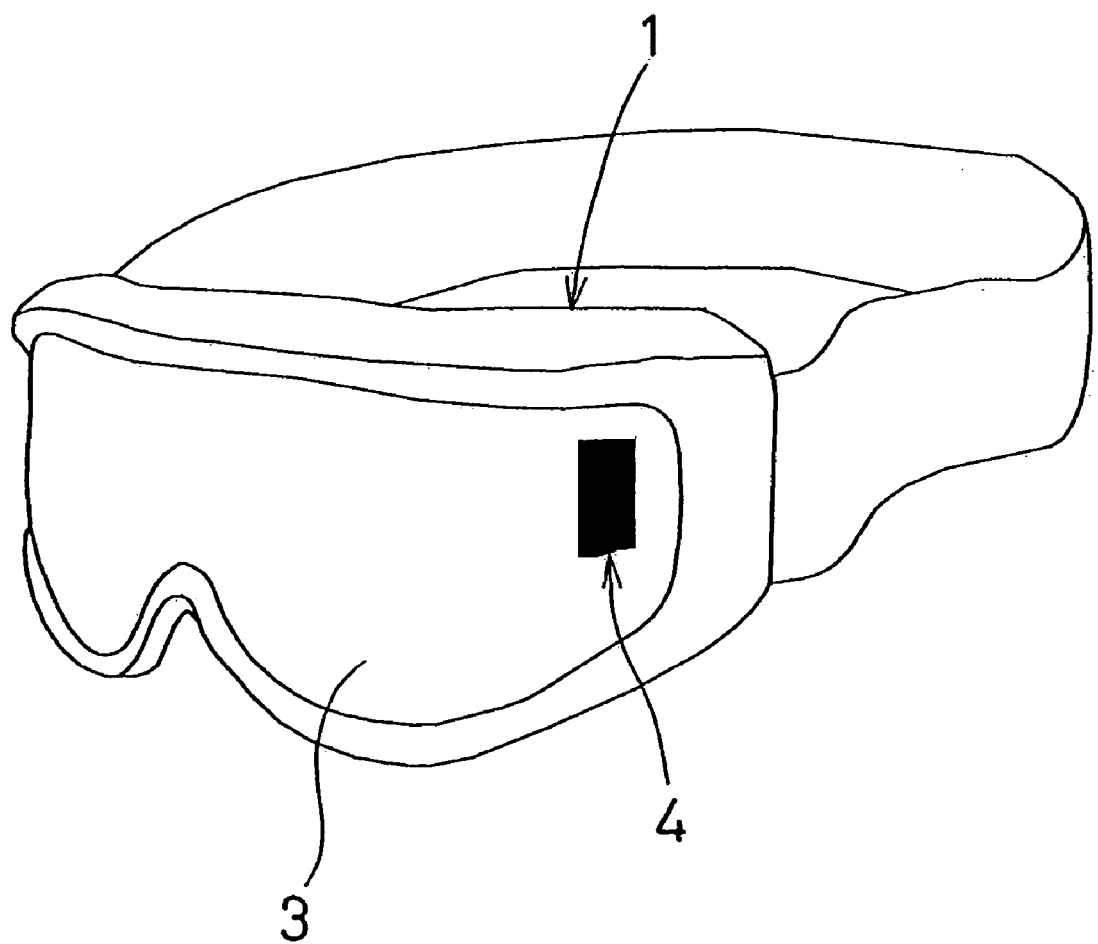
FIG. 5 is a perspective view showing another embodiment where a pair of sports goggles of the present invention is applied to a pair of motorcycle goggles.

A pair of sports goggles of the present invention shown in FIG. 5 is used as a pair of motorcycle goggles. The pair of goggles has a goggle main body 1, an information processing means 2 and an information display means 4. The information processing means 2 is mounted on the inner portion of the goggle main body 1 and the information display means 4 is mounted on a lens which is an eyepiece portion 3 of the goggle main body 1. The information processing means 2 and the information display means 4 of this pair of goggles are treated to be vibration-proofed, drip-proofed and so on in order to make this goggles operational while a user's motorcycle is running The information processing means 2 has a sensing function to check physiological information, the velocity of wind, the speed, the revolution speed of the engine and so on. It also has an information communicating means for transmitting and receiving data instantly, and the information communicating means has a system for communicating with other outside transmitting and receiving devices.

Figure 6:
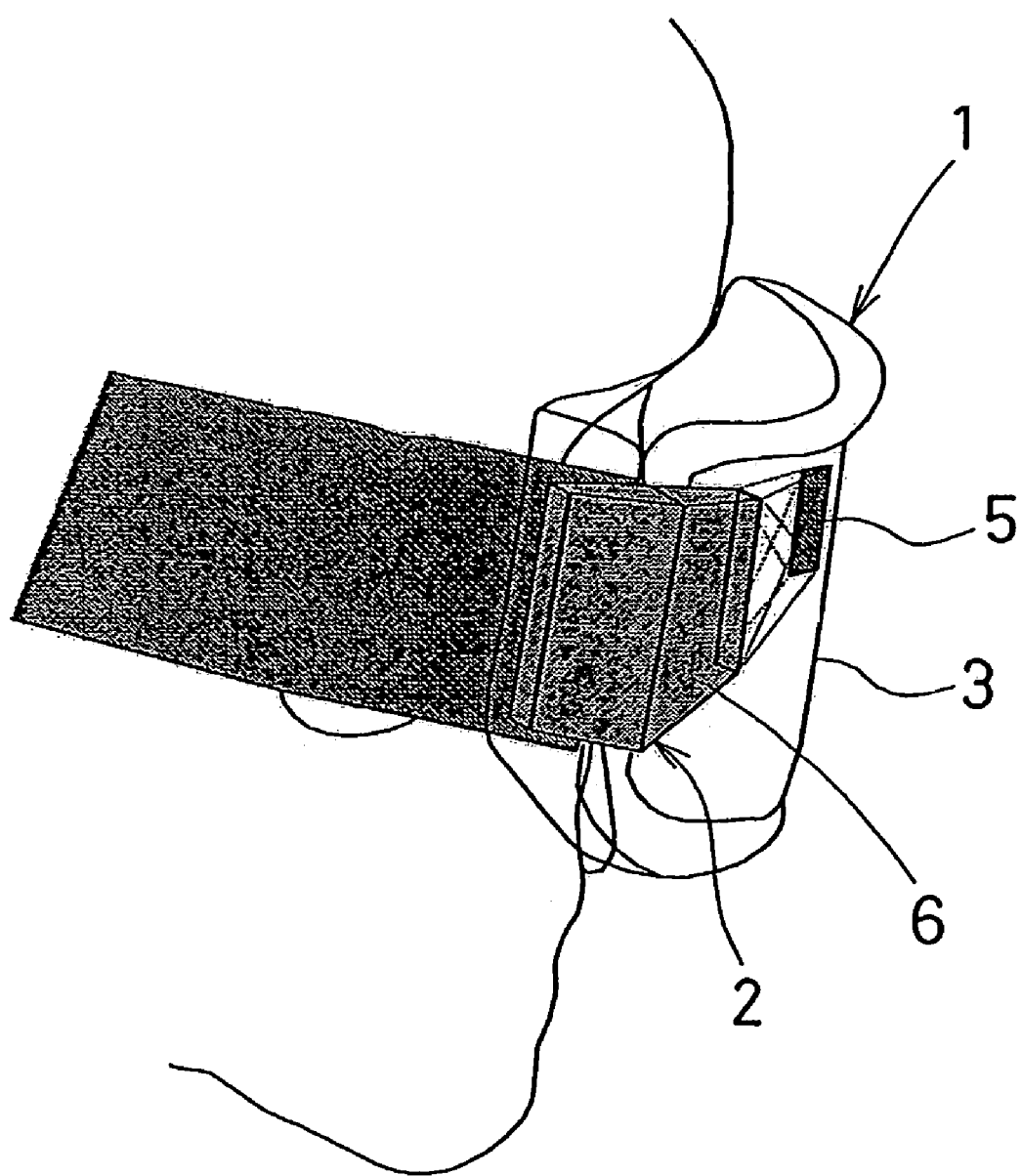
FIG. 6 is a diagrammatic perspective view showing the display principle of an information display means of a pair of sports goggles according to the present invention.
Figure 7:
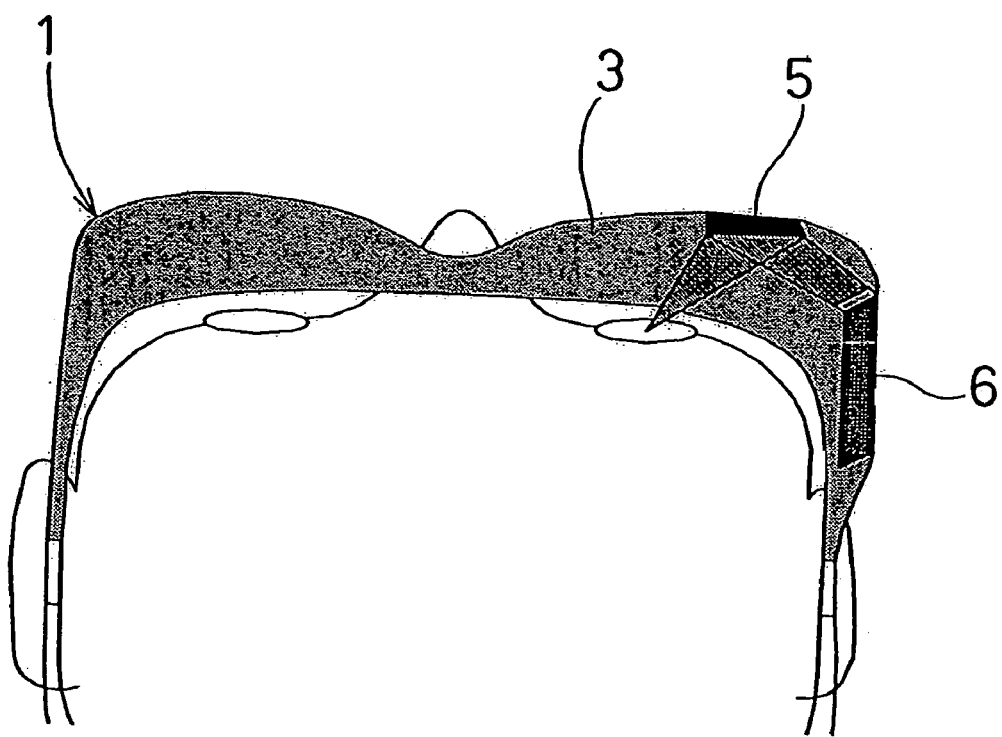
FIG. 7 is a diagrammatic plane view showing the display principle of an information display means of a pair of sports goggles according to the present invention.

As shown in FIGS. 6 and 7, the information display means 4 has a HOE 5 which is integrally molded on the eyepiece portion 3 and a compact-sized DMD 6 placed on the goggle main body 1 so that the information projected by light which the compact-sized DMD 6 receives from a compact-sized light source is made to be visible.

These features enable plural drivers to share the information while driving each motorcycle and/or to share information with the fellow passenger if there is, so that it can be helpful to drive cooperatively.

A pair of sports goggles of the present invention has the above-mentioned structures so that a user can check the displayed information according to need so as to get timely appropriate information in a relatively short time, can focus on the display without affecting the play and can receive detailed instructions from instructors and/or coaches while playing sports.

The invention claimed is:

1. A pair of sports goggles comprising:
a goggle main body,
an information processing means mounted on the goggle main body, and
an information display means mounted on an eyepiece portion of the goggle main body; and
further comprising an information communicating means of transmitting and receiving information to and from the outside, wherein:
the information communicating means is mounted on the goggle main body;
said information processing means includes means for sensing physiological information and displays said physiological information on said information display means;
said received information received by said information communicating means is further displayed on said information display means;
the information processing means is a microcomputer housing a central processing unit, a random access memory, a read-only memory and a power source of a secondary cell therein; and
the information processing means has a navigation system using undersea topographic information which is stored in the memory.

2. A pair of sports goggles comprising:
a goggle main body,
an information processing means mounted on the goggle main body, and
an information display means mounted on an eyepiece portion of the goggle main body; and
further comprising an information communicating means of transmitting and receiving information to and from the outside, wherein;
the information communicating means is mounted on the goggle main body;
said information processing means includes means for sensing physiological information and displays said physiological information on said information display means; and
said received information received by said information communicating means is further displayed on said information display means; and
image data for reproducing virtual space is loaded into the information processing means, and the image data is displayed by the information display means.

3. The pair of sports goggles according to claim 2, wherein the information processing means and the information display means are integrally formed.

4. The pair of sports goggles according to claim 2, wherein the information display means includes a display device and an optical device.

5. The pair of sports goggles according to claim 4, wherein the display device is any one of a liquid crystal, a cathode ray tube, a semiconductor device, a light-emitting diode, an electroluminescence and a digital micromirror device, and the optical device is any one of a mirror, a prism, a lens and a holographic optical element.

6. The pair of sports goggles according to claim 5, wherein the information display means includes a laminating of the holographic optical element on a surface of the eyepiece and the liquid crystal panel placed inside of the goggle main body so that information displayed on this liquid crystal panel is visible.

7. The pair of sports goggles according to claim 5, wherein the information display means includes the holographic optical element which is insert-molded on a surface of the eyepiece portion and the liquid crystal panel placed inside of the goggle main body so that information displayed on this liquid crystal panel is visible.

8. The pair of sports goggles according to claim 5, wherein the information display means includes the lens which is integrally molded on a surface of the eyepiece portion and the compact-sized cathode ray tube placed outside of the goggle main body so that information displayed by this compact-sizes cathode ray tube is visible.

9. The pair of sports goggles according to claim 2, wherein the information communicating means is any one of a digital radio and an analog radio.

10. The pair of sports goggles according to claim 9, wherein the information communicating means has a system which instantly transmits and receives data and communicates with an outside transmitting and receiving device.

11. A pair of sports goggles comprising:
a goggle main body,
an information processing means mounted on the goggle main body, and
an information display means mounted on an eyepiece portion of the goggle main body; and
further comprising an information communicating means of transmitting and receiving information to and from the outside, wherein;
the information communicating means is mounted on the goggle main body;
said information processing means includes means for sensing physiological information and displays said physiological information on said information display, means; and
said received information received by said information communicating means is further displayed on said information display means;
the information display means includes a display device and an optical device;
the display device is any one of a liquid crystal, a cathode ray tube, a semiconductor device, a light-emitting diode,an electroluminescence and a digital micromirror device;
the optical device is any one of a mirror, a prism, a lens and a holographic optical element;
the information display means includes the holographic optical element which is integrally molded on a surface of the eyepiece portion; and
the compact-sized digital micromirror element is placed on the goggle main body so that information projected by light which the compact-sized digital micromirror element receives from a compact-sized light source is visible.

* * * * *